(12) United States Patent
Yamayose et al.

(10) Patent No.: US 10,234,413 B2
(45) Date of Patent: Mar. 19, 2019

(54) ELECTRONIC DEVICE, ABNORMALITY DETERMINATION METHOD, AND COMPUTER PROGRAM PRODUCT

(71) Applicant: KABUSHIKI KAISHA TOSHIBA, Tokyo (JP)

(72) Inventors: Yuu Yamayose, Tokyo (JP); Tetsuya Kugimiya, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 212 days.

(21) Appl. No.: 15/074,499

(22) Filed: Mar. 18, 2016

(65) Prior Publication Data
US 2016/0282291 A1    Sep. 29, 2016

(30) Foreign Application Priority Data
Mar. 27, 2015 (JP) ................... 2015-066462

(51) Int. Cl.
| | |
|---|---|
| G01N 17/00 | (2006.01) |
| G01R 19/257 | (2006.01) |
| G01N 27/20 | (2006.01) |
| G01N 27/04 | (2006.01) |
| H05K 3/30 | (2006.01) |

(52) U.S. Cl.
CPC .......... G01N 27/20 (2013.01); G01N 27/045 (2013.01); H05K 3/30 (2013.01)

(58) Field of Classification Search
CPC ......... G01N 27/20; G01N 27/045; H05K 3/30
USPC ................. 324/693, 750.3; 702/58
See application file for complete search history.

(56) References Cited

U.S. PATENT DOCUMENTS

| | | | |
|---|---|---|---|
| 8,413,525 B1 * | 4/2013 | Schultz ................. | B25B 23/14 73/862.21 |
| 2013/0124118 A1 * | 5/2013 | Monda ................ | G01R 31/048 702/58 |
| 2014/0052392 A1 | 2/2014 | Bernstein et al. | |

FOREIGN PATENT DOCUMENTS

| | | |
|---|---|---|
| JP | 3265197 | 3/2002 |
| JP | 2009-257863 | 11/2009 |
| JP | 2011-146510 | 7/2011 |
| JP | 4812856 | 11/2011 |
| JP | 2013-015542 | 1/2013 |
| JP | 2013-26349 A | 2/2013 |
| JP | 2013-104843 | 5/2013 |
| JP | 2013-145824 | 7/2013 |

* cited by examiner

*Primary Examiner* — Farhana Hoque
(74) *Attorney, Agent, or Firm* — Finnegan, Henderson, Farabow, Garrett & Dunner, L.L.P.

(57) ABSTRACT

According to one embodiment, an electronic device comprises a circuit board, an electrical component, and a measurement unit. The circuit board has a first face. The electrical component includes a second face electrically connected to the first face via a bonding material, a first end in a first direction along the second face, and a second end. The second end is opposite to the first end in the first direction. The measurement unit is configured to measure a characteristic changing depending on a conductivity of the bonding material. A first distance between the first face and the first end is shorter than a second distance between the first face and the second end. The measurement unit includes a first measurement unit configured to measure the characteristic of a part of the bonding material. The part is adjacent to the first end.

16 Claims, 10 Drawing Sheets

ELECTRONIC DEVICE, ABNORMALITY DETERMINATION METHOD, AND COMPUTER PROGRAM PRODUCT

CROSS-REFERENCE TO RELATED APPLICATION(S)

This application is based upon and claims the benefit of priority from Japanese Patent Application No. 2015-066462, filed on Mar. 27, 2015; the entire contents of which are incorporated herein by reference.

FIELD

Embodiments described herein relate generally to an electronic device, an abnormality determination method, and a computer program product.

BACKGROUND

Conventionally, there has been known an electronic component which detects an abnormality of a bonding portion between the electronic component and a substrate based on a change in an electrical resistance.

It is beneficial to obtain a novel electronic device that can reduce disadvantage such as an electronic device which can detect an abnormality of a bonding portion with higher efficiency.

DETAILED DESCRIPTION

In general, according to one embodiment, an electronic device comprises a circuit board, an electrical component, and a measurement unit. The circuit board has a first face. The electrical component includes a second face electrically connected to the first face via a bonding material, a first end in a first direction along the second face, and a second end. The second end is opposite to the first end in the first direction. The measurement unit is configured to measure a characteristic changing depending on a conductivity of the bonding material. A first distance between the first face and the first end is shorter than a second distance between the first face and the second end. The measurement unit includes a first measurement unit configured to measure the characteristic of a part of the bonding material. The part is adjacent to the first end.

Hereinafter, exemplary embodiments of the present invention will be disclosed. Configurations and control of embodiments (technical feature) to be illustrated hereinafter, and action and results (effects) to be obtained through the configurations and control are examples. Further, a plurality of the embodiments to be exemplified hereinafter include the same components. Hereinafter, the same or similar components will be attached with the common reference numerals, and the redundant description thereof will be omitted. Incidentally, a direction S is a direction along a face (first face) of a board, a direction H is a normal direction of the face of the board, and a direction S1 is a direction along a face (second face) of an electrical component in the respective drawings.

First Embodiment

Figure 1:
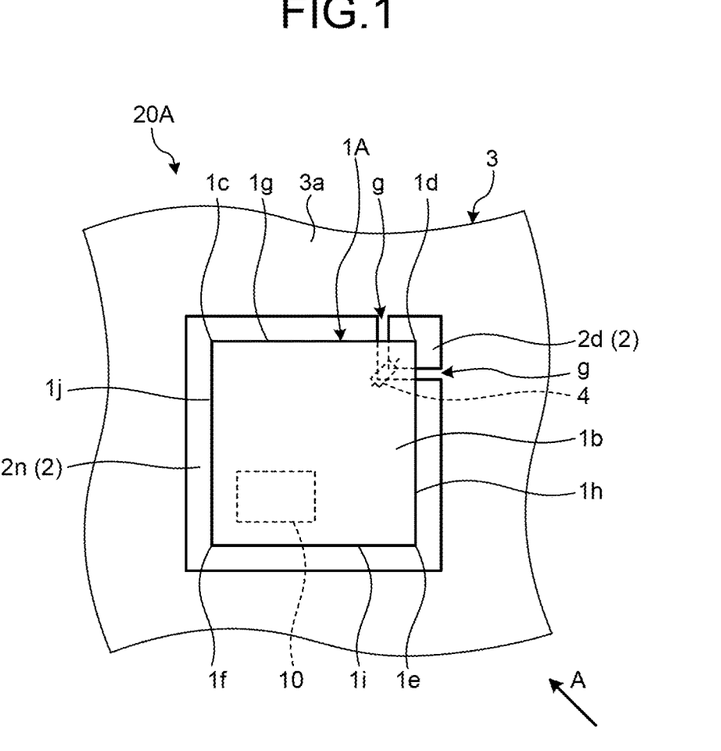
FIG. 1 is a schematic and exemplary plan view of an electronic device according to a first embodiment.
Figure 2:
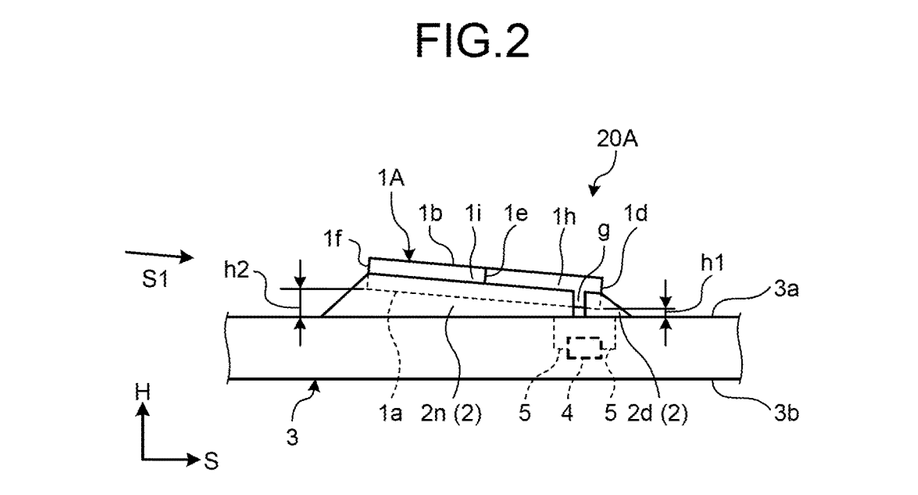
FIG. 2 is a schematic and exemplary side view of the electronic device according to the first embodiment.

An electronic device 20A according to a first embodiment, illustrated in FIGS. 1 to 4, includes a board 3 (substrate) and an electrical component 1A. The electrical component 1A is, for example, a semiconductor element (die), and is bonded onto the board 3 via a bonding material 2 by die bonding. At least one electrode (part electrode) (not illustrated) is disposed on a face 1a of the electrical component 1A. Further, at least one electrode (board electrode) (not illustrated) is disposed on a face 3a of the board 3 which faces the face 1a. The bonding material 2 is disposed between these two electrodes, and allows the electrodes to be bonded to each other electrically and mechanically. Accordingly, the electrical component 1A and the board 3 are bonded to each other electrically and mechanically. The bonding material 2 may be various types of bonding materials of, for example, a solder paste, a silver paste, a bonding material containing intermetallic compound with a high heat resistance, a bonding material for metal particle sinter bonding, and the like. Incidentally, FIGS. 1 and 2 illustrate a state in which the electrical component 1A is bonded onto the board 3 via the bonding material 2, but the electrical component 1A may be bonded further with a wire (not illustrated), or the electrical component 1A may be coated with a coating material (not illustrated). Further, the electronic device 20A may include another component to be mounted to the board 3, and the like. The board 3 is an example of a circuit board. The face 3a is an example of a first face. The face 1a is an example of a second face.

The board 3 is configured in a plate shape or a film shape, and includes the face 3a and a face 3b which is opposite to the face 3a. An insulating base of the board 3 may include, for example, a synthetic resin material, ceramic, or the like. Further, the face 3a and 3b or the board 3 includes a conductor portion (a conductor pattern, an electrode, a pad, a wiring layer, or the like) (not illustrated). The board 3 may be a build-up substrate, a coreless substrate, or the like. Further, the board 3 may be a rigid substrate, a flexible substrate, or the like. Further, the board 3 is provided with a through-hole, a via, a through electrode, or the like. Further, the board 3 may be an interposer, a substrate, a package substrate, or the like. The board 3 can be referred to as a support portion or a heat radiating portion.

The electrical component 1A may be, for example, an integrated circuit such as a system on a chip (SoC), a central processing unit (CPU), or the like, may be a switching element such as a metal oxide semiconductor field effect transistor (MOS-FET), an insulated gate bipolar transistor (IGBT), or may be another semiconductor component (semiconductor part) or an element. The electrical component 1A generates heat by its own operation. In this case, the electrical component 1A can be referred to also as a heat generator. Further, the electrical component 1A sometimes receives heat from an external heat generator.

The electrical component 1A is configured in a flat cuboid shape, for example. In this embodiment, as illustrated in FIGS. 1 and 2, the electrical component 1A includes the face 1a and 1b. The face 1a and 1b have quadrilateral shape. The face 1b is positioned opposite to the face 1a. The direction H is perpendicular to the direction S along the faces 1a and 1b. The direction H can be referred to as a thickness direction. Further, the shape of the electrical component 1A is quadrilateral when viewed in a direction perpendicular to the face 3a of the board 3 (in the direction H), and includes four corners 1c to 1f and four sides 1g to 1j as illustrated in FIG. 1. The corners 1c to 1f and the sides 1g to 1j can be referred to as end portions. Further, the sides 1g to 1j are also faces (side faces) of the electrical component 1A as illustrated in FIG. 2. Incidentally, FIG. 1 illustrates the quadrilateral shape of the electrical component 1A when viewed in a direction perpendicular to the face 3a of the board 3, but the shape of the electrical component 1A is also quadrilateral when viewed in a direction perpendicular to the direction S1 along the face 1a of the electrical component 1A. The direction perpendicular to the face 1a is an example of a second direction.

As illustrated in FIG. 2, the face 3a of the board 3 and the face 1a of the electrical component 1A are not parallel to each other in this embodiment, and the electrical component 1A is mounted onto the face 3a of the board 3 in an inclined state (posture). To be specific, the corner 1d, which is one of the two corners 1d and 1f to be arranged diagonally to each other, is positioned closer to the face 3a of the board 3 than the other corner 1f. That is, a distance h1 between the corner 1d and the face 3a is shorter than a distance h2 between the corner 1f and the face 3a. The corner 1d is an example of a first end, the corner 1f is an example of a second end, the distance h1 is an example of a first distance, the distance h2 is an example of a second distance.

The bonding material 2 includes a part (bonding portion 2d) adjacent to the corner 1d and another part (bonding portion 2n). The bonding portion 2d and the bonding portion 2n are arranged with a gap g disposed therebetween. When viewed perpendicular to the face 3a of the board 3 as illustrated in FIG. 1, the gap g is positioned closer to the corner 1d than the corners 1c, 1e and 1f. Further, the gap g is arranged such that the part (the bonding portion 2d) adjacent to the corner 1d in the bonding material 2 is separated from the bonding portion 2n by the gap g. That is, the bonding portion 2d is positioned closer to the corner 1d than the bonding portion 2n, the bonding portion 2d has a smaller volume than the bonding portion 2n, and the bonding portion 2d has a lower height from the face 3a of the board 3 than the bonding portion 2n. The bonding portion 2d is an example of a first bonding portion, and the bonding portion 2n is an example of a second bonding portion.

According to such a configuration, it is possible to use the bonding portion 2d to detect a failure symptom with respect to generation of a defect caused by a thermal load and the like. In a case in which a temporal change in temperature of the electronic device 20A by heat generation in the electrical component 1A, a peripheral component or the like, for example, stress is generated or increased in the bonding material 2 due to a difference in linear expansion coefficient of materials of the electrical component 1A, the bonding material 2, and the board 3. There are various types of loads including a tensile load, a compressive load, a shear load, and the like, and various types of stress accompanying the load include a tensile stress, a compressive stress, a shear stress, and the like in this case, but stress increases in general in a case in which the bonding material 2 is thin, as compared to a case in which the bonding material 2 is thick, and accordingly, a crack caused by thermal fatigue is likely to occur. Accordingly, it is possible to determine an abnormality prior to occurrence of failure by providing the thin part (the bonding portion 2d) and the thick part (the bonding portion 2n) in the bonding material 2, and measuring a characteristic of the thin part (the bonding portion 2d) by setting the face 1a of the electrical component 1A to be inclined with respect to the face 3a of the board 3 as in this embodiment.

The characteristic of the bonding portion 2d is measured by a measurement unit 4. As illustrated in FIG. 2, the measurement unit 4 and a conductor portion 5 electrically connect the bonding portion 2d and the bonding portion 2n. Further, the bonding portions 2d and 2n are electrically connected to each other via a pad (not illustrated), an internal wiring, or the like in the electrical component 1A. That is, a circuit is provided connecting the measurement unit 4 back to itself via the right part of the conductor portion 5 in FIG. 2, the bonding portion 2d, the electrical component 1A, the bonding portion 2n, and the left part of the conductor portion 5 in FIG. 2. Accordingly, it is possible to measure a change in electrical resistance of the bonding portion 2d accompanying the generation of the crack, the breakage, or the like by the measurement unit 4. Incidentally, a change in electrical resistance in a case in which the bonding portion 2n is broken is also measured by the measurement unit 4, but it is not necessary to consider erroneous detection of such an event because a probability that the abnormality occurs in the bonding portion 2n earlier than in the bonding portion 2d is low due to the difference in thickness between the bonding portion 2d and 2n, or because a probability that the bonding portion 2n is turned into the state of conduction failure in overall is extremely low. Since the bonding portion 2d and the bonding portion 2n are disposed to be separated from each other with the gap g therebetween in this embodiment, it is possible to configure the above-described electric circuit, and accordingly, the measurement of the electrical resistance of the bonding portion 2d by the measurement unit 4 is realized. The electrical resistance is an example of an electrically characteristic, and the measurement unit 4 is an example of a first measurement unit.

The configuration in which the bonding portion 2d and the bonding portion 2n are separated with the gap g therebetween may be obtained, for example, by separating electrodes (not illustrated) on the face 3a of the board 3 with the gap therebetween, and the bonding material 2 is divided and placed on the separated electrodes. Further, the configuration may be obtained by, for example, coating a position to which the gap g on the face 3a of the board 3 is provided with resist in advance before coating the face 3a of the board 3 with the bonding material 2. However, a method of providing the gap g is not limited to the above-described method.

Further, the configuration in which the electrical component 1A is mounted onto the face 3a of the board 3 in the inclined state may be obtained by, for example, putting a weight on the corner 1d of the electrical component 1A during the bonding process of the bonding material 2 by reflow or the like. Further, the configuration may be obtained also by setting the coating amount (height) of the bonding material 2 to be different by locations of the electrodes on the face 3a of the board 3. An inclination angle (angle between an arrow S and an arrow S1 in FIG. 2) of the electrical component 1A is required to have a degree that is likely to cause the abnormality in the bonding portion 2d earlier than in the bonding portion 2n, and is set according to a dimension of the electrical component 1A. To be specific, it is possible to expect the effect when the inclination angle is equal to or larger than 1°, for example.

Figure 3:
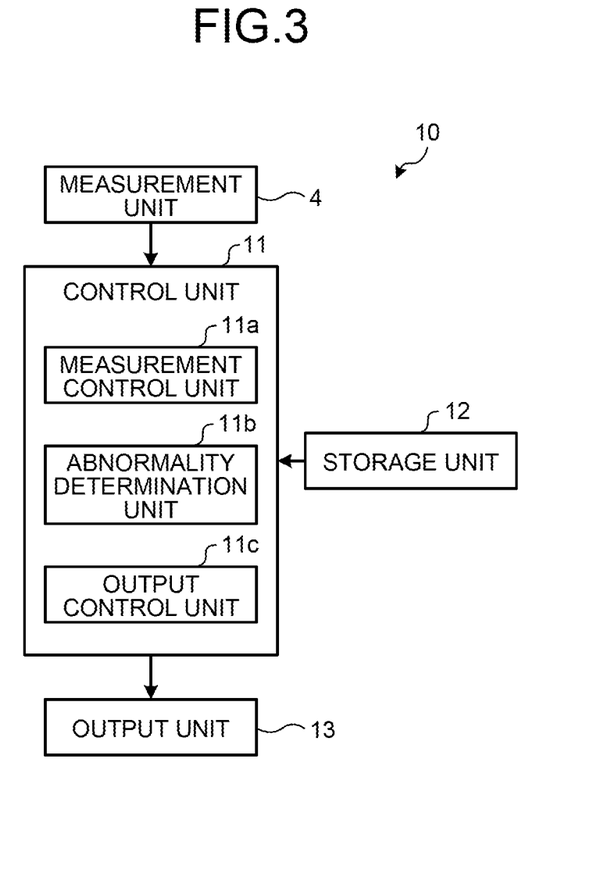
FIG. 3 is a schematic and exemplary block diagram of a control circuit of the electronic device according to the first embodiment.

The electronic device 20A may include at least a part of a control circuit 10 as illustrated in FIG. 3. The control circuit 10 includes a control unit 11, a storage unit 12, an output unit 13, and the like. The control unit 11 includes a measurement control unit 11a, an abnormality determination unit 11b, an output control unit 11c, and the like. The measurement control unit 11a controls the measurement unit 4 so as to measure. The abnormality determination unit 11b determines the abnormality based on a measurement result of the measurement unit 4. The output control unit 11c controls the output unit 13 so as to output information, which indicates the occurrence of the abnormality, for example, in a case in which the abnormality determination unit 11b determines that the abnormality is present.

The control unit 11 is, for example, a central processing unit (CPU), a controller, or the like. The CPU can execute various types of arithmetic processing according to loaded programs (for example, an operating system (OS), application, firmware, and the like). In this embodiment, the control unit 11 functions as the respective units illustrated in FIG. 3 (the measurement control unit 11a, the abnormality determination unit 11b, the output control unit 11c, and the like) by the execution of the arithmetic processing according to the programs, for example. The program includes a module for execution of each function of the measurement control unit 11a, the abnormality determination unit 11b, the output control unit 11c, and the like. Incidentally, the programs can be provided as each file in an installable form or an executable form being recorded in a recording medium which is readable by a computer, such as a CD-ROM, a FD, a CD-R, a DVD, or the like. Further, the program can be recorded in a storage unit of a computer which is connected to a communication network, and introduced by being downloaded via the network. Further, the program can be incorporated in advance in the ROM, or the like.

The storage unit 12 is a non-volatile storage unit, for example. Threshold data to be used to determine the abnormality in the abnormality determination unit 11b, data of the program to cause the control unit 11 to execute the arithmetic processing, and the like can be stored in the storage unit 12. The output unit 13 is, for example, a display, a speaker, and the like, and is controlled by the output control unit 11c to execute output of information such as information indicating the occurrence of the abnormality, and the like. Incidentally, the output unit 13 may transmit data to another electronic component or another electronic device. The control circuit 10 may be provided in an electronic component different from the electrical component 1A of the electronic device 20A, or may be included in a part of the electrical component 1A illustrated in FIG. 1. Further, the storage unit 12 and the output unit 13 may be included in the electronic device 20A, or may be a different electronic device.

Figure 4:
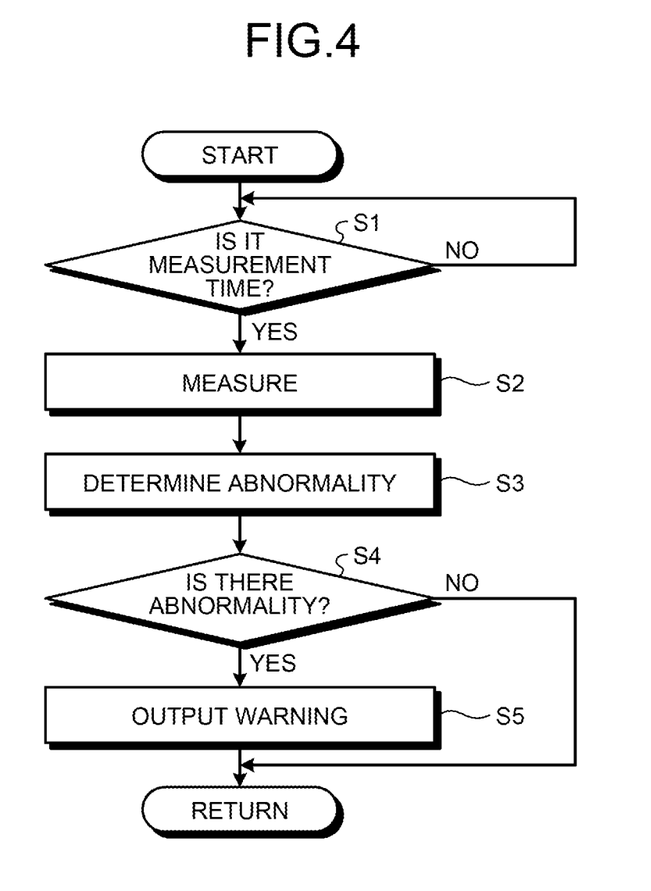
FIG. 4 is an exemplary flowchart of an arithmetic processing according to the control circuit of the electronic device according to the first embodiment.

As exemplified in FIG. 4, when it is the measurement time to be set in advance (Yes in S1), the control unit 11 functions as the measurement control unit 11a and controls the measurement unit 4 so as to measure (S2). Next, the control unit 11 functions as the abnormality determination unit 11b, compares the measurement result according to the measurement unit 4 with the threshold stored in the storage unit 12, and determines presence or absence of the abnormality (S3). For example, in a case in which the measurement unit 4 measures an electrical resistance, the abnormality determination unit 11b can determine the case with the electrical resistance measured by the measurement unit 4 exceeding the threshold as an abnormality state. In a case in which the abnormality occurs (Yes in S4), the control unit 11 functions as the output control unit 11c, and can control the output unit 13 so as to output the information indicating the occurrence of the abnormality (S5). Incidentally, the process of FIG. 4 returns to S1 in the case of No in S1, and the process ends in the case of No in S4. Further, the flow of FIG. 4 can be repeatedly executed. Incidentally, the flow in which the measurement is executed at the measurement time set in advance has been described herein, but the measurement may be executed at a specific manipulation such as power-ON or power-OFF of the electronic device.

In this embodiment described above, the electrical component 1A is mounted onto the face 3a of the board 3 such that the electrical component 1A is inclined on the face 3a of the board 3, that is, the distance h1 (the first distance) between the face 3a of the board 3 (the first face) and the corner 1d (the first end) is shorter than the distance h2 (the second distance) between the face 3a and the corner 1f (the second end). Accordingly, it is possible to provide the part on which the crack is generated earlier or the part which is broken earlier than the other part of the bonding material 2, that is, the bonding portion 2d in the bonding material 2. Accordingly, it is possible to more efficiently or more accurately capture the abnormality or a sign thereof of the bonding material 2 when the measurement unit 4 measures the characteristic of the bonding portion 2d. Accordingly, it is possible to grasp the generation (the sign) of the abnormality and take a measure before the entire bonding material 2 is broken, for example. Incidentally, the sign of the abnormality can be measured by setting a threshold different from the threshold at which the breakage occurs, and for example, by setting the threshold lower than the threshold of the case of the breakage in the case of the electrical resistance.

Further, the corner 1d (the first end), which is one of the two corners 1d and 1f diagonally opposing each other, is close to the face 3a of the board 3 than the other corner 1f (the second end) in this embodiment. Accordingly, one point of the corner 1d of the electrical component 1A is close to the face 3a of the board 3, and thus, it is possible to more easily provide the thin part, that is the bonding portion 2d (the first bonding portion) in the bonding material 2.

Further, the electrical component 1A includes only the measurement unit 4 which is adjacent to the corner 1d, and measures the characteristic of the bonding portion 2d in this embodiment. Accordingly, it is possible to reduce the number of the measurement units 4, and it is easy to reduce labor or cost required for manufacture. Further, since the number of the measurement units 4 is a few, it is possible to easily improve a degree of freedom in design of the electrical component 1A as compared to a case in which the number of the measurement units 4 is many.

Second Embodiment

Figure 5:
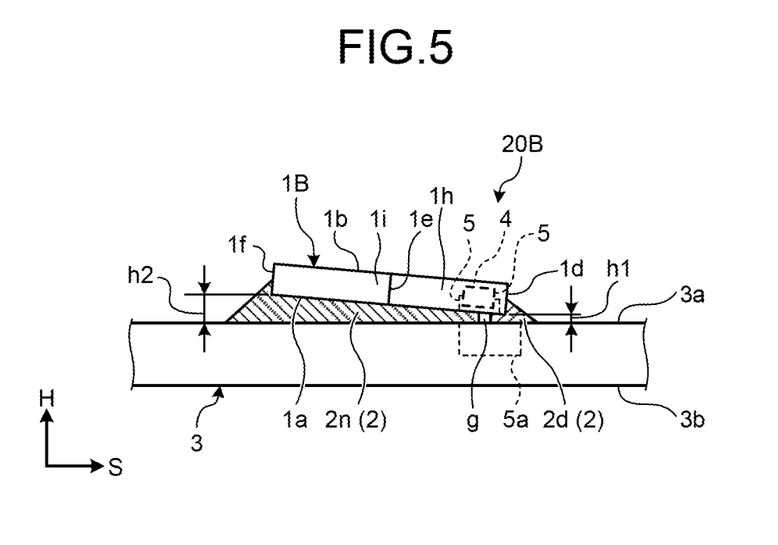
FIG. 5 is a schematic and exemplary side view of an electronic device according to a second embodiment.

An electrical component 1B and an electronic device 20B according to a second embodiment illustrated in FIG. 5 have the same configurations as the electrical component 1A and the electronic device 20A according to the first embodiment described above. Accordingly, it is possible to obtain the same action and effect based on the same configurations according to this embodiment, too. However, the measurement unit 4 is disposed in the electrical component 1B, and a conductor portion 5a (wiring), which electrically connects the bonding portion 2d and the bonding portion 2n, is disposed inside the board 3. In this embodiment, a circuit is provided connecting the measurement unit 4 back to itself via the left part of the conductor portion 5 in FIG. 5, the bonding portion 2n, the conductor portion 5a inside the board 3, the bonding portion 2d, and the right part of the conductor portion 5 in FIG. 5. Accordingly, it is possible to measure the change of the electrical resistance (characteristic) of the bonding portion 2d accompanying the generation of the crack, the breakage, or the like by the measurement unit 4 according to this embodiment, too.

Third Embodiment

Figure 6:
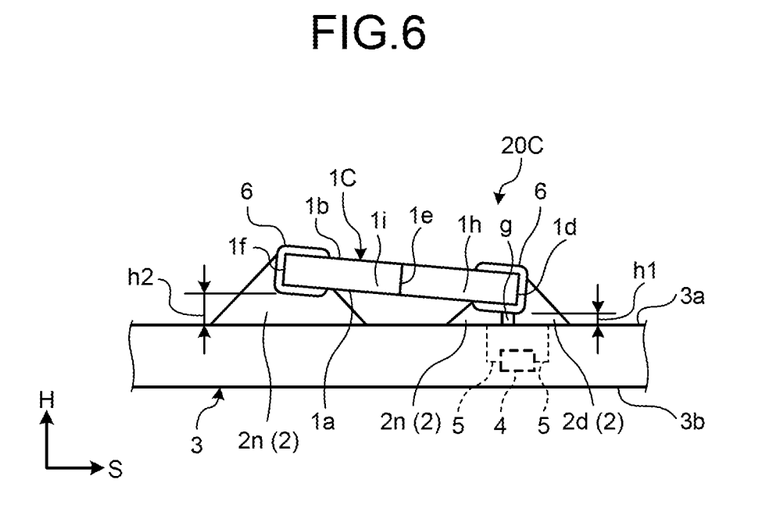
FIG. 6 is a schematic and exemplary side view of an electronic device according to a third embodiment.

An electrical component 1C and an electronic device 20C according to a third embodiment illustrated in FIG. 6 have the same configurations as the electrical component 1A and the electronic device 20A according to the first embodiment described above. Accordingly, it is possible to obtain the same action and effect based on the same configurations according to this embodiment, too. However, the electrical component 1C is a chip part, and conductor portions 6 (electrode) disposed in the corners 1d and 1f and an electrode of the face 3a of the board 3 are electrically connected to each other via the bonding material 2 in this embodiment. Similarly to the first embodiment described above, it is possible to cause the electrical component 1C to be inclined also in this case by setting the distance h1 between the corner 1d and the face 3a of the board 3 to be shorter than the distance h2 between the corner 1f and the face 3a of the board 3 at the opposite side. Further, it is possible to measure the change of the electrical resistance (characteristic) of the bonding portion 2d accompanying the generation of the crack or the breakage by the measurement unit 4 in a circuit similar to that of FIG. 2 which includes the bonding portions 2d and 2n separated by the gap g.

Fourth Embodiment

Figure 7:
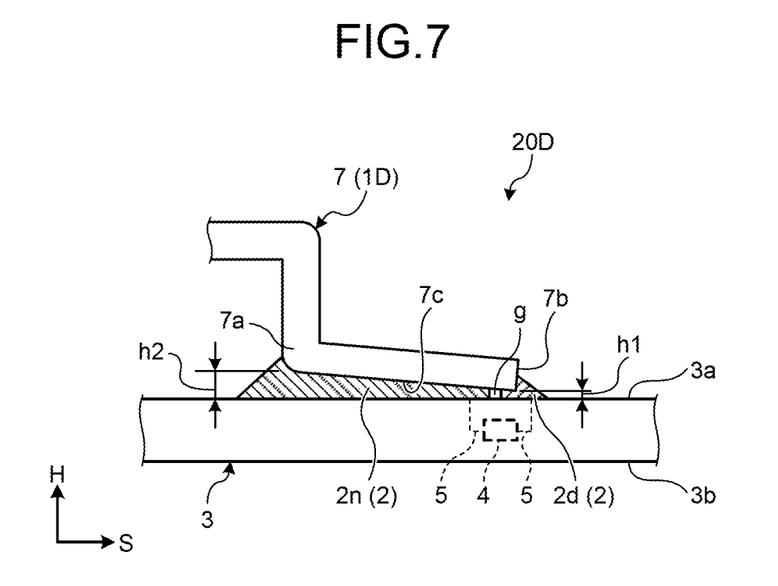
FIG. 7 is a schematic and exemplary side view of an electronic device according to a fourth embodiment.

An electrical component 1D and an electronic device 20D according to a fourth embodiment illustrated in FIG. 7 have the same configurations as the electrical component 1A and the electronic device 20A according to the first embodiment described above. Accordingly, it is possible to obtain the same action and effect based on the same configurations according to this embodiment, too. However, the electrical component 1D is a so-called gullwing-type electrical component, and a conductor portion 7 (lead) and an electrode of the face 3a of the board 3 are electrically connected to each other by the bonding material 2 in this embodiment. In this case, the conductor portion 7 includes a part (section) between a bent portion 7a (end) at a base side and an tip end portion 7b with a face 7c to be bonded such that a distance h1 between the tip end portion 7b (end) and the face 3a of the board 3 is shorter than a distance h2 between the bent portion 7a and the face 3a of the board 3. Further, the bonding portion 2d separated with the gap g is electrically connected to the end portion 7b similarly to the first embodiment described above. Accordingly, it is possible to measure the change of the electrical resistance (characteristic) of the bonding portion 2d accompanying the generation of the crack or the breakage by the measurement unit 4 in a circuit similar to that of FIG. 2 which includes the bonding portions 2d and 2n separated by the gap g in this embodiment, too.

Fifth Embodiment

Figure 8:
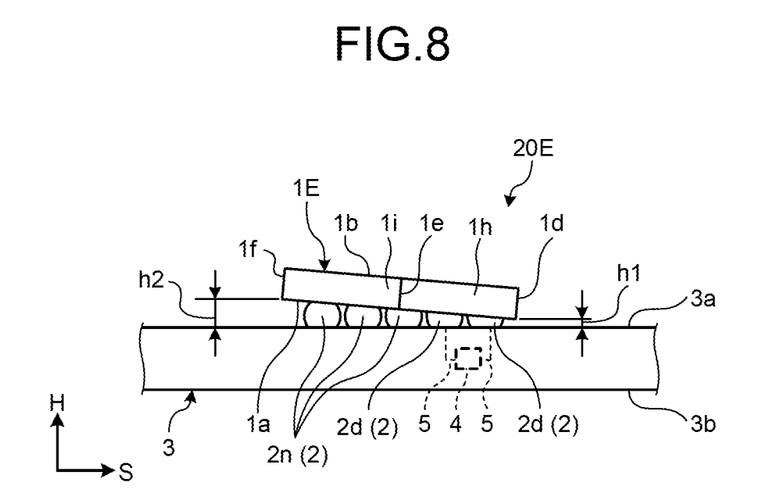
FIG. 8 is a schematic and exemplary side view of an electronic device according to a fifth embodiment.

An electrical component 1E and an electronic device 20E according to a fifth embodiment illustrated in FIG. 8 have the same configurations as the electrical component 1A and the electronic device 20A according to the first embodiment described above. Accordingly, it is possible to obtain the same action and effect based on the same configurations according to this embodiment, too. However, the electrical component 1E is a ball grid array (BGA), and an electrode of the electrical component 1E and an electrode of the face 3a of the board 3 are electrically connected to each other via a plurality of the bonding materials 2. The bonding material 2 is a bump. The bonding portion 2d is a test unit (dummy bump) for measurement which is not used in transmission of an electrical signal or power to be generally used in the electrical component 1E. In this embodiment, a circuit is provided connecting the measurement unit 4 back to itself via the right side of the conductor portion 5 in FIG. 8, the bonding portion 2d, a pad of the electrical component 1E, and a conductor portion such as an internal wiring, the bonding portion 2d, and the left side of the conductor portion 5 in FIG. 8. Accordingly, it is possible to measure the change of the electrical resistance (characteristic) of the bonding portion 2d accompanying the generation of the crack, the breakage, or the like by the measurement unit 4 according to this embodiment, too.

Sixth Embodiment

Figure 9:
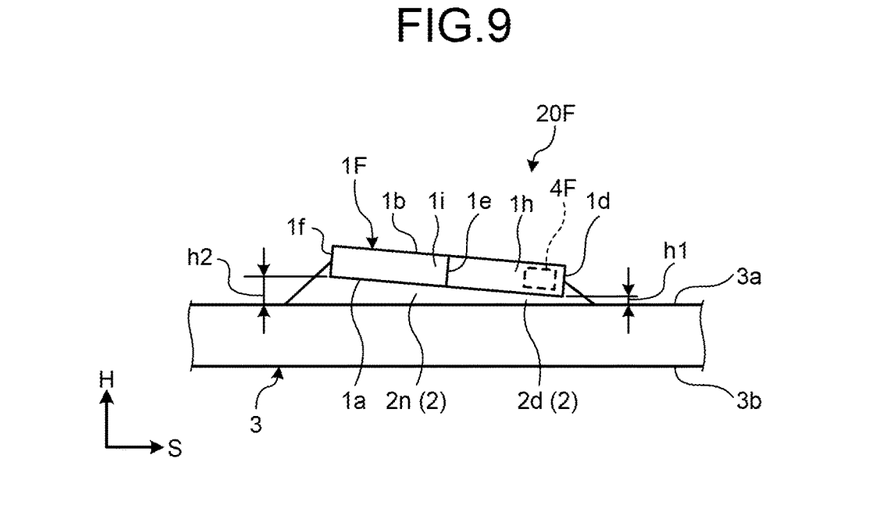
FIG. 9 is a schematic and exemplary side view of an electronic device according to a sixth embodiment.

An electrical component 1F and an electronic device 20F according to a sixth embodiment illustrated in FIG. 9 have the same configurations as the electrical component 1A and the electronic device 20A according to the first embodiment described above. Accordingly, it is possible to obtain the same action and effect based on the same configurations according to this embodiment, too. However, a measurement unit 4F to measure temperature is disposed instead of the measurement unit 4 to measure the electrical resistance in this embodiment. The bonding material 2 has a thermal conductivity as well as an electrical conductivity. Accordingly, a heat radiation performance from the bonding portion 2d deteriorates when the crack or the breakage occurs in the thin part (the bonding portion 2d) adjacent to the corner 1d. Accordingly, it is possible to measure the change in temperature characteristic accompanying the crack and the breakage by measuring temperature and the change of the temperature over time by the measurement unit 4F. In regard to the measurement of the temperature, it is unnecessary to separate the bonding material 2, which is different from the measurement of the electrical resistance. However, the bonding material 2 may be separated with the gap g, and the heat radiation performance in the part adjacent to the bonding portion 2d of the same configuration as the first embodiment may be measured by the measurement unit 4F. In the case of the temperature characteristic, it is possible to determine that it is the abnormal state in a case in which the temperature is equal to or higher than a threshold, or in a case in which the speed of the change in the temperature is equal to or lower than a threshold. Incidentally, a location of the measurement unit 4F can be suitably changed.

Seventh Embodiment

Figure 10:
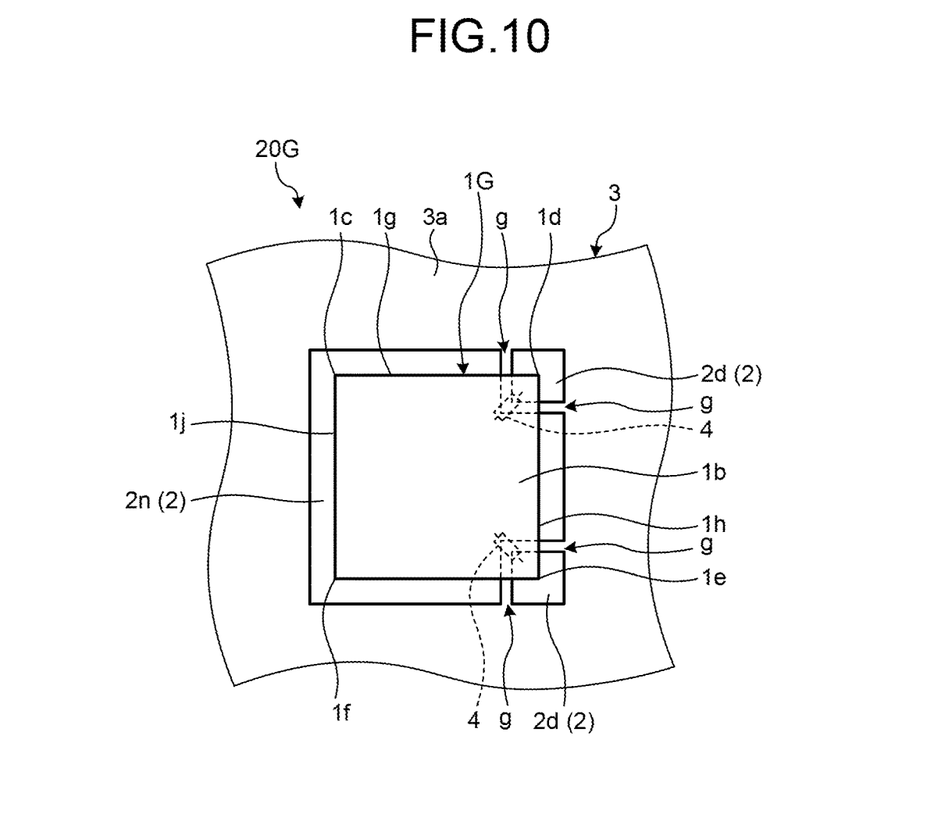
FIG. 10 is a schematic and exemplary plan view of an electronic device according to a seventh embodiment.

An electrical component 1G and an electronic device 20G according to a seventh embodiment illustrated in FIG. 10 have the same configurations as the electrical component 1A and the electronic device 20A according to the first embodiment described above. Accordingly, it is possible to obtain the same action and effect based on the same configurations according to this embodiment, too. However, two bonding portions 2d are disposed to be adjacent to the corner 1d and the corner 1e, in other words, to be adjacent to a side 1h in this embodiment. In this case, a distance between the side 1h and the face 3a of the board 3 is shorter than a distance between the side 1j and the face 3a of the board 3. According to this embodiment, it is easy to enhance the accuracy or the reliability of the abnormality determination according to the change of the electrical resistance (characteristic) of the bonding portion 2d as compared to the case in which only the single measurement unit 4 is disposed. Further, the side 1h, wider than the corner 1d, becomes a lower side of the inclination according to this embodiment, and thus, it is easy to set an inclination state of the electrical component 1G to be more stable when the electrical component 1G is bonded to the face 3a of the board 3 by the bonding material 2 in the state of being inclined. The side 1h is an example of the first end, and the side 1j is an example of the second end.

Eighth Embodiment

Figure 11:
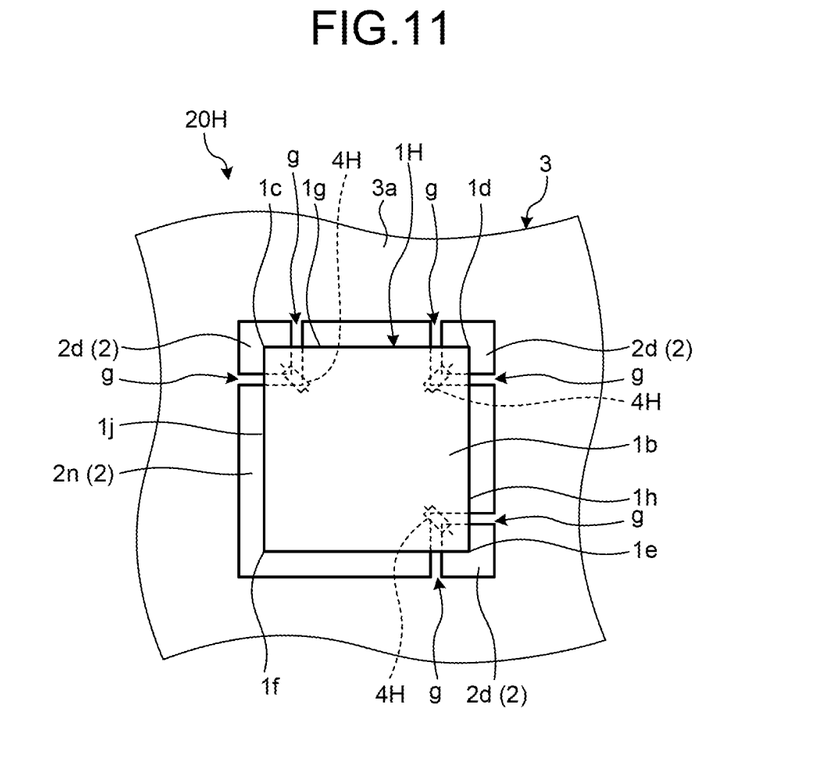
FIG. 11 is a schematic and exemplary plan view of an electronic device according to an eighth embodiment.

An electrical component 1H and an electronic device 20H according to an eighth embodiment illustrated in FIG. 11 have the same configurations as the electrical component 1A and the electronic device 20A according to the first embodiment described above. Accordingly, it is possible to obtain the same action and effect based on the same configurations according to this embodiment, too. However, three bonding portions 2d are disposed to be adjacent to the corner 1c and the corner 1e in addition to the corner 1d in this embodiment. However, the four corners 1c to 1f are disposed such that a distance between the corner 1d and the face 3a of the board 3 is the shortest (shortest value), a distance between the corner 1f and the face 3a of the board 3 is the longest (longest value), and a distance between the corner 1c and the face 3a of the board 3 and a distance between the corner 1e and the face 3a of the board 3 are intermediate values. In this embodiment, the measurement unit 4H measures a characteristic of the bonding portion 2d adjacent to the corner 1c and the corner 1d, which are different from the corner 1d (the first end) and the corner 1f (the second end). Accordingly, the measurement unit 4H is an example of the second measurement unit. It is easy to enhance the accuracy or the reliability of the abnormality determination according to the change of the electrical resistance (characteristic) of the bonding portion 2d as compared to the case in which only the single measurement unit 4 is disposed according to this embodiment, too.

Ninth Embodiment

Figure 12:
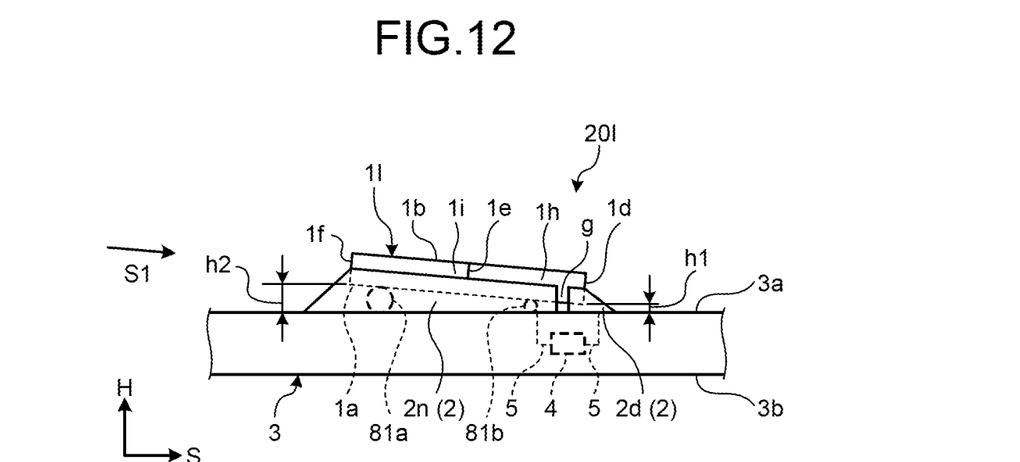
FIG. 12 is a schematic and exemplary side view of an electronic device according to a ninth embodiment.

An electrical component 1I and an electronic device 20I according to a ninth embodiment illustrated in FIG. 12 have the same configurations as the electrical component 1A and the electronic device 20A according to the first embodiment described above. Accordingly, it is possible to obtain the same action and effect based on the same configurations according to this embodiment, too. However, adjustment members 81a and 81b are interposed between the face 3a of the board 3 and the face 1a of the electrical component 1I in this embodiment. The adjustment members 81a and 81b are balls (spheres) made of metal which are not melted in the bonding process, for example, and a diameter of the adjustment member 81a is larger than a diameter of the adjustment member 81b. The adjustment members 81a and 81b can be arranged to a predetermined position on the face 3a of the board 3, and temporarily held or fixed prior to the bonding process using the bonding material 2. In the bonding process of the electrical component 1I and the board 3, the face 3a of the board 3 in a state in which the adjustment members 81a and 81b are arranged is coated with the bonding material 2 in the state with liquidity before being fixed, and thereafter, the bonding material 2 is fixed by the reflow or the like. According to this embodiment, it is easy to reduce a variation in posture (inclination) of the electrical component 1I by the adjustment members 81a and 81b. Incidentally, the number of the adjustment members 81a and 81b is not limited to two, and may be one or three or more. Further, various types of the arrangement of the adjustment members 81a and 81b on the face 3a can be set. The adjustment members 81a and 81b can be referred to also as a height adjustment member, an postural adjustment member, an inclination adjustment member, a positioning member, or the like. Incidentally, the bonding material 2 may be a bonding material such as a solder paste containing a metal ball in advance may be used instead of the postural adjustment using the metal ball.

Tenth Embodiment

Figure 13:
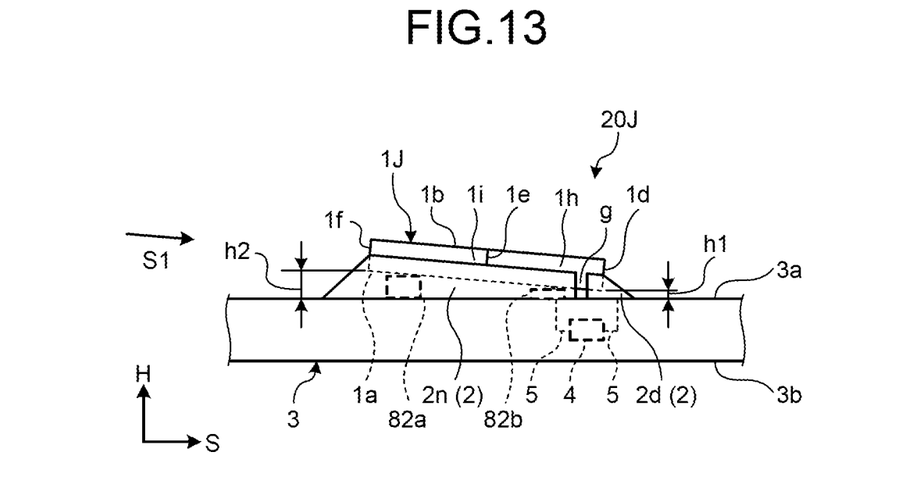
FIG. 13 is a schematic and exemplary side view of an electronic device according to a tenth embodiment.

An electrical component 1J and an electronic device 20J according to a tenth embodiment illustrated in FIG. 13 have the same configurations as the electrical component 1A and the electronic device 20A according to the first embodiment described above. Accordingly, it is possible to obtain the same action and effect based on the same configurations according to this embodiment, too. However, adjustment members 82a and 82b are interposed between the face 3a of the board 3 and the face 1a of the electrical component 1J in this embodiment. Each function and manufacturing method of the adjustment members 82a and 82b is the same as those of the adjustment members 81a and 81b according to the ninth embodiment described above. However, the adjustment members 82a and 82b are provided not in a spherical shape, but in a columnar shape or a flat shape in this embodiment. Shapes of the adjustment members 82a and 82b in a direction perpendicular to the face 3a of the board 3, when viewed in a plan view, can be set to various types of shapes such as a circular shape and a quadrilateral shape. It is possible to obtain the same effect as the ninth embodiment described in this embodiment, too. Incidentally, the adjustment member may be provided to be integrated with the board 3, or may be provided to be integrated with the electrical component 1J.

Eleventh Embodiment

Figure 14:
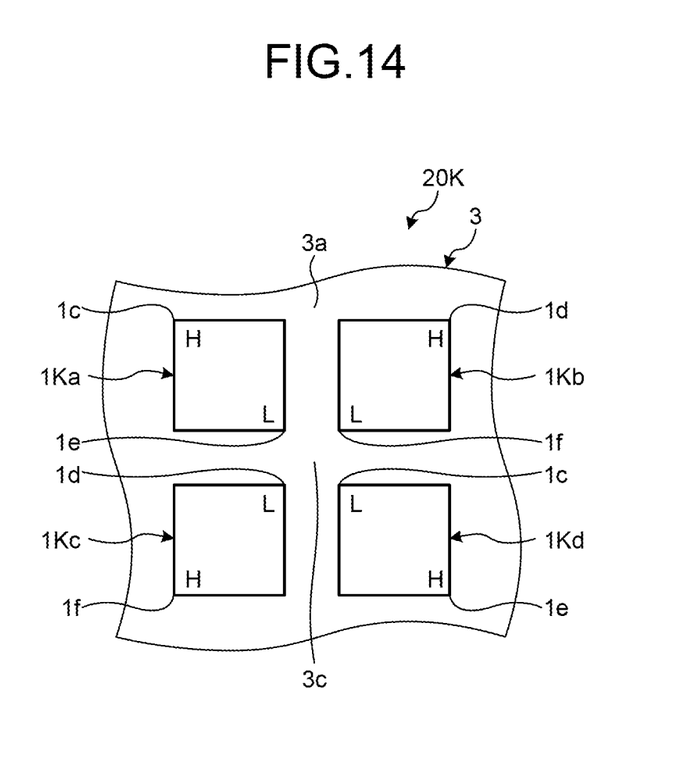
FIG. 14 is a schematic and exemplary plan view of an electronic device according to an eleventh embodiment.

Electrical components 1Ka to 1Kd and an electronic device 20K according to an eleventh embodiment illustrated in FIG. 14 have the same configurations as the electrical component 1A and the electronic device 20A according to the first embodiment described above. Accordingly, it is possible to obtain the same action and effect based on the same configurations according to this embodiment, too. However, the electronic device 20K includes the four electrical components 1Ka to 1Kd in this embodiment. The four electrical components 1Ka to 1Kd are arranged in an inclination state such that the corners 1c to 1f, close to a center portion 3c (center of gravity) of a plurality of the electrical components 1Ka to 1Kd in a plan view of the face 3a of the board 3, is closer to the face 3a of the board 3 than the other corners of the electrical components 1Ka to 1Kd. In FIG. 14, reference letter L indicates the first end (corner), and reference letter H indicates the second end (corner). Further, the arrangement of the corners 1c to 1f and the sides 1g to 1j of the electrical components 1Ka to 1Kd is the same as that of the electrical component 1A according to the first embodiment in FIG. 1. That is, the corner 1e of the electronic component 1Ka, the corner 1f of the electronic component 1Kb, the corner 1d of the electronic component 1Kc, and the corner 1c of the electronic component 1Kd are examples of the first end, and the corner 1c of the electronic component 1Ka, the corner 1d of the electronic component 1Kb, the corner 1f of the electronic component 1Kc, and the corner 1e of the electronic component 1Kd are examples of the second end in this embodiment. In a case in which the plurality of electrical components 1Ka to 1Kd are arranged at positions relatively close to each other in this manner, temperature at the center position (the center portion 3c) in the arrangement of the plurality of electrical components 1Ka to 1Kd is likely to increase. A change in the temperature is more likely to increase at the position at which the temperature increases, and a thermal load accompanying the temperature change is likely to increase. Accordingly, it is easy to enhance the accuracy or the reliability in the abnormality determination using the change of the electrical resistance (characteristic) of the bonding portion 2d according to such a configuration.

Twelfth Embodiment

Figure 15:
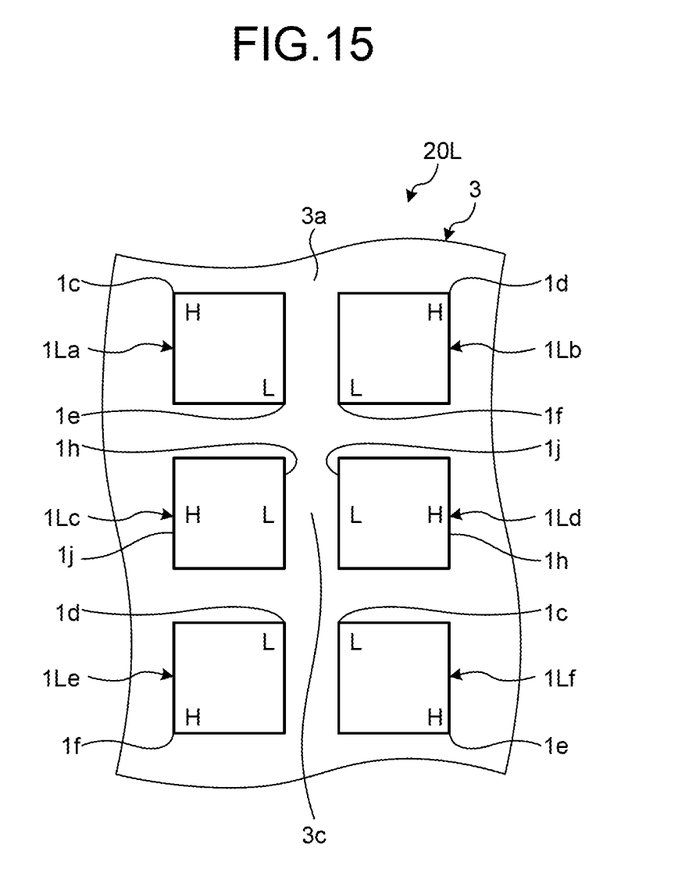
FIG. 15 is a schematic and exemplary plan view of an electronic device according to a twelfth embodiment.

Electrical components 1La to 1Lf and an electronic device 20L according to a twelfth embodiment illustrated in FIG. 15 have the same configurations as the electrical component 1A and the electronic device 20A according to the first embodiment described above. Accordingly, it is possible to obtain the same action and effect based on the same configurations according to this embodiment, too. However, the electronic device 20L includes the six electrical components 1La to 1Lf in this embodiment. In this embodiment, similarly to the eleventh embodiment, the six electrical components 1La to 1Lf are arranged with an inclination state such that the corners 1c to 1f or the sides 1h and 1j, close to the center portion 3c (center of gravity) of a plurality of the electrical components 1La to 1Lf in a plan view of the face 3a of the board 3, is closer to the face 3a of the board 3 than the other corners or sides of the electrical components 1La to 1Lf. In FIG. 15, reference letter L indicates the first end (the corner or the side), and reference letter H indicates the second end (the corner or the side). Further, the arrangement of the corners 1c to 1f and the sides 1g to 1j of the electrical components 1La to 1Lf is the same as that of the electrical component 1A according to the first embodiment in FIG. 1. That is, the corner 1e of the electronic component 1La, the corner 1f of the electronic component 1Lb, the side 1h of the electronic component 1Lc, and the side 1j of the electronic component 1Ld, the corner 1d of the electronic component 1Le, the corner 1c of the electronic component 1Lf are examples of the first end, and the corner 1c of the electronic component 1La, the corner 1d of the electronic component 1Lb, the side 1j of the electronic component 1Lc, the side 1h of the electronic component 1Ld, and the corner 1f of the electronic component 1Le, and the corner 1e of the electronic component 1Lf are examples of the second end in this embodiment. In a case in which the plurality of electrical components 1La to 1Lf are arranged at positions relatively close to each other in this manner, temperature at the center position (the center portion 3c) in the arrangement of the plurality of electrical components 1La to 1Lf is likely to increase. A change in the temperature is more likely to increase at the position at which the temperature increases, and a thermal load accompanying the temperature change is likely to increase. Accordingly, it is easy to enhance the accuracy or the reliability in the abnormality determination using the change of the electrical resistance (characteristic) of the bonding portion 2d according to such a configuration.

Thirteenth Embodiment

Figure 16:
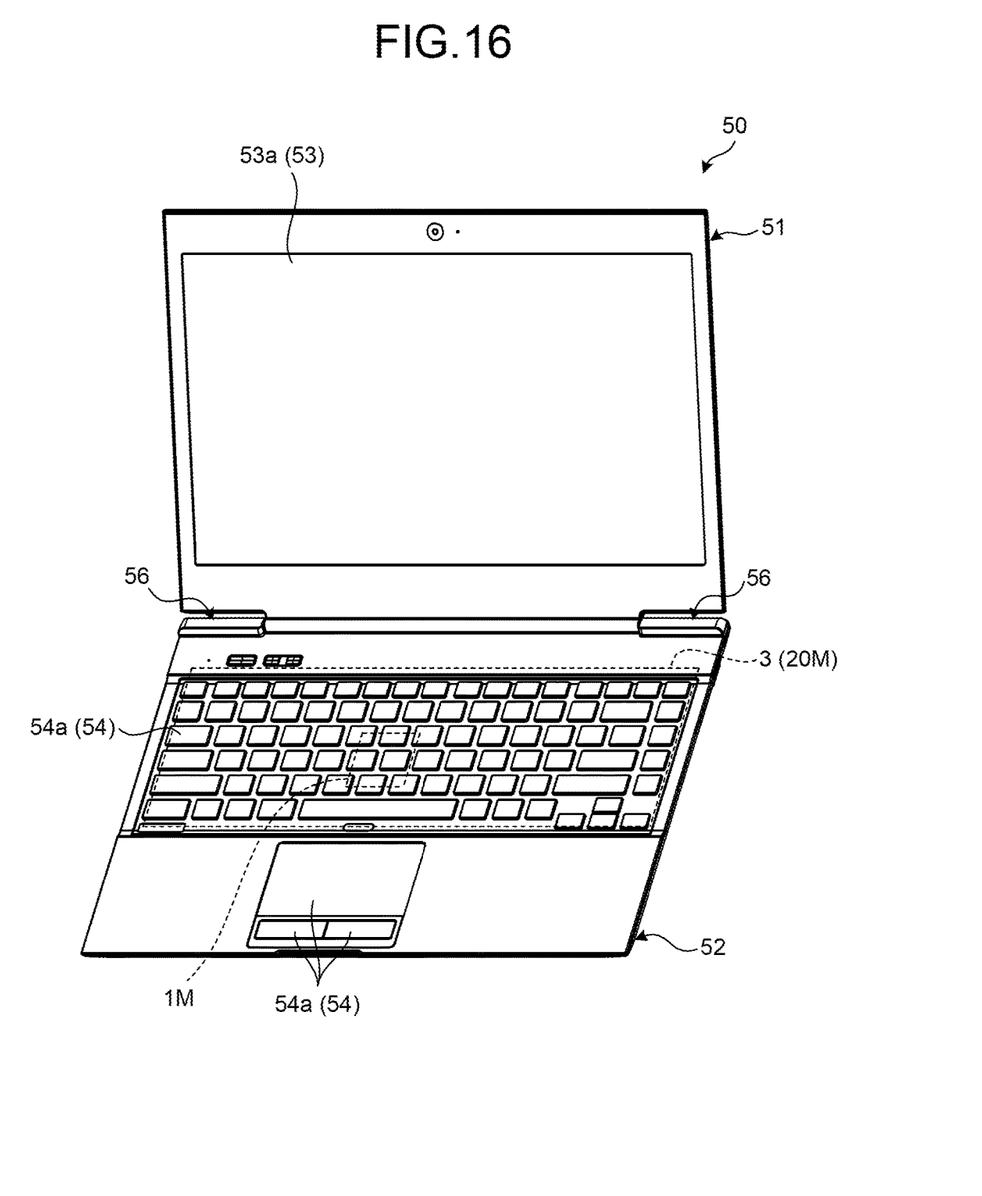
FIG. 16 is a schematic and exemplary perspective view of an electronic device according to a thirteenth embodiment.

An electrical component 1M and an electronic device 20M according to a thirteenth embodiment illustrated in FIG. 16 have the same configurations as the electrical component 1A and the electronic device 20A according to the first embodiment described above. Accordingly, it is possible to obtain the same action and effect based on the same configurations according to this embodiment, too. However, the electronic device 20M housed in a housing 52 and the housing 52 configures an electronic device 50 in this embodiment. The electronic device 50 includes the housings 51 and 52, a display 53, and an input device 54, and the like. The housing 51 and the housing 52 are connected to each other to be rotatable via a hinge 56. The display 53 is housed in the housing 51 in a state in which a display surface 53a thereof is exposed, and the input device 54 is housed in the housing 52 in a state in which an input unit 54a thereof is exposed. The display 53 (the output unit) is, for example, a liquid crystal display (LCD), an organic electro luminescent display (OELD), or the like. The input device 54 is, for example, a keyboard, a pointing device, a click button, or the like. The electronic device 20M is provided with a speaker (output unit) (not illustrated). Further, the housing 52 houses the electrical component 1M according to this embodiment, configured as a CPU, for example, and the board 3 on which an electronic component such as a controller (not illustrated) is mounted. Incidentally, the electrical component 1M may be an electrical component other than the CPU. Further, the electronic device is not limited to a clamshell personal computer, but may be a desktop personal computer, or another electronic device.

Moreover, the various modules of the systems described herein can be implemented as software applications, hardware and/or software modules, or components on one or more computers, such as servers. While the various modules are illustrated separately, they may share some or all of the same underlying logic or code.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An electronic device comprising:
    a circuit board having a first face;
    an electrical component including a second face electrically connected to the first face via a bonding material, a first end in a first direction along the second face, and a second end being opposite to the first end in the first direction; and
    a measurement unit configured to measure a characteristic changing depending on a conductivity of the bonding material, wherein
    a first distance between the first face and the first end is shorter than a second distance between the first face and the second end, and
    the measurement unit includes a first measurement unit configured to measure the characteristic of a part of the bonding material, the part being adjacent to the first end.

2. The electronic device according to claim 1, wherein
    the electrical component as seen from a second direction is quadrilateral and includes four corners,
    the second direction is perpendicular to the second face,
    the first end is one of two corners arranged diagonally opposing each other among the four corners, and
    the second end is the other of the two corners.

3. The electronic device according to claim 2, wherein the measurement unit includes only the first measurement unit.

4. The electronic device according to claim 2, wherein the measurement unit includes a second measurement unit configured to measure the characteristic of a part of the bonding material, the part being adjacent to a corner different from the first end and the second end among the four corners.

5. The electronic device according to claim 4, wherein the measurement unit includes only the first measurement unit and the second measurement unit.

6. The electronic device according to claim 1, wherein
    the electrical component as seen from a second direction is quadrilateral and includes four sides,
    the second direction is perpendicular to the second face,
    the first end is one of two sides spaced apart from each other among the four sides, and
    the second end is the other of the two sides.

7. The electronic device according to claim 1, wherein the bonding material includes a first bonding portion adjacent to the first end and a second bonding portion arranged with a gap against the first bonding portion.

8. The electronic device according to claim 1, comprising:
    an adjustment member disposed between the first face and the second face.

9. The electronic device according to claim 1, wherein the characteristic represents an electrical characteristic.

10. The electronic device according to claim 1, wherein the characteristic represents a temperature characteristic.

11. The electronic device according to claim 1, wherein the measurement unit is disposed in the circuit board.

12. The electronic device according to claim 1, wherein the measurement unit is disposed in the electrical component.

13. The electronic device according to claim 1, wherein the first end is positioned closer to a position at which a temperature change of the circuit board is larger than the temperature change of the circuit board at the second end.

14. The electronic device according to claim 1, comprising:
    a housing housing the circuit board, the electrical component, and the measurement unit.

15. An abnormality determination method performed by an electronic device having a circuit board, an electrical component, and a measurement unit, the circuit board including a first face, the electrical component including a second face, a first end, and a second end, the second face electrically connected to the first face via a bonding material, the first end being an end in a first direction along the second face, the second end being opposite to the first end in the first direction, the measurement unit being configured to measure a characteristic changing depending on a conductivity of the bonding material, the abnormality determination method comprising:
    measuring the characteristic changing depending on the conductivity of a part of the bonding material, the part being adjacent to the first end; and
    determining the abnormality based on the measured characteristic.

16. A computer program product including programmed instructions embodied in and stored on a non-transitory computer readable medium, wherein the instructions, when executed by a computer, cause the computer to perform an abnormality determination method of an electronic device, the electronic device having a circuit board, an electrical component, and a measurement unit, the circuit board including a first face, the electrical component including a second face, a first end, and a second end, the second face electrically connected to the first face via a bonding material, the first end being an end in a first direction along the second face, the second end being opposite to the first end in the first direction, the measurement unit being configured to measure a characteristic changing depending on a conductivity of the bonding material, the computer program product cause the computer to perform;
    measuring the characteristic changing depending on the conductivity of a part of the bonding material, the part being adjacent to the first end; and
    determining an abnormality based on the measured characteristic.

* * * * *